(12) United States Patent
Fleischer et al.

(10) Patent No.: US 8,747,930 B2
(45) Date of Patent: Jun. 10, 2014

(54) SILICEOUS PARTICLES

(75) Inventors: Daniel Fleischer, Oakland, CA (US); Andrew Thompson, Oakland, CA (US); Marko Jukic, San Francisco, CA (US); Guido Radaelli, Oakland, CA (US)

(73) Assignee: Aurora Algae, Inc., Hayward, CA (US)

( * ) Notice: Subject to any disclaimer, the term of this patent is extended or adjusted under 35 U.S.C. 154(b) by 94 days.

(21) Appl. No.: 12/494,170

(22) Filed: Jun. 29, 2009

(65) Prior Publication Data

US 2010/0330658 A1    Dec. 30, 2010

(51) Int. Cl.
*C12C 3/00* (2006.01)

(52) U.S. Cl.
USPC ............................................... 426/425

(58) Field of Classification Search
USPC ............................................... 426/425
See application file for complete search history.

(56) References Cited

U.S. PATENT DOCUMENTS

| | | |
|---|---|---|
| 1,926,780 A | 9/1933 | Lippincott |
| 2,730,190 A | 1/1956 | Brown |
| 2,766,203 A | 10/1956 | Brown |
| 3,175,687 A | 3/1965 | Jones |
| 3,468,057 A | 9/1969 | Buisson |
| 3,897,000 A | 7/1975 | Mandt |
| 3,962,466 A | 6/1976 | Nakabayashi |
| 4,003,337 A | 1/1977 | Moore |
| 4,159,944 A | 7/1979 | Erickson |
| 4,253,271 A | 3/1981 | Raymond |
| 4,267,038 A | 5/1981 | Thompson |
| 4,341,038 A | 7/1982 | Bloch et al. |
| 4,365,938 A | 12/1982 | Warinner |
| 4,535,060 A | 8/1985 | Comai |
| 4,658,757 A | 4/1987 | Cook |
| 5,105,085 A | 4/1992 | McGuire et al. |
| 5,130,242 A | 7/1992 | Barclay |
| 5,180,499 A | 1/1993 | Hinson |
| 5,244,921 A * | 9/1993 | Kyle et al. ............ 514/560 |
| 5,275,732 A | 1/1994 | Wang |
| 5,338,673 A | 8/1994 | Thepenier et al. |
| 5,478,208 A | 12/1995 | Kasai |
| 5,527,456 A | 6/1996 | Jensen |
| 5,539,133 A | 7/1996 | Kohn |
| 5,567,732 A * | 10/1996 | Kyle et al. ............ 514/560 |
| 5,658,767 A | 8/1997 | Kyle |
| 5,661,017 A | 8/1997 | Dunahay et al. |

(Continued)

FOREIGN PATENT DOCUMENTS

| | | |
|---|---|---|
| JP | 09-024362 A | 1/1997 |
| JP | 2004300218 A | 10/2001 |

(Continued)

OTHER PUBLICATIONS

Cravatto et al., Improved extraction of vegetable oils under high-intensity ultrasound and/or microwaves, Ultrasonics Sonochemistry 15:898-902 (2008).*

(Continued)

*Primary Examiner* — Jezia Riley
(74) *Attorney, Agent, or Firm* — Carr & Ferrell LLP (57) ABSTRACT

Various aspects provide for extracting siliceous particles. Siliceous particles may include or be derived from diatoms. Certain embodiments provide for segregating suspensions into two or more segregation products. In some cases, a first product includes siliceous particles, and a second product may include hydrophobic species. Certain aspects provide for extracting non-siliceous biomass (e.g., lipids).

19 Claims, 4 Drawing Sheets

(56) References Cited

U.S. PATENT DOCUMENTS

| | | | |
|---|---|---|---|
| 5,668,298 | A | 9/1997 | Waldron |
| 5,776,349 | A | 7/1998 | Guelcher et al. |
| 6,117,313 | A | 9/2000 | Goldman |
| 6,143,562 | A | 11/2000 | Trulson et al. |
| 6,166,231 | A * | 12/2000 | Hoeksema ............... 554/12 |
| 6,372,460 | B1 | 4/2002 | Gladue et al. |
| 6,524,486 | B2 | 2/2003 | Borodyanski |
| 6,579,714 | B1 | 6/2003 | Hirabayashi et al. |
| 6,736,572 | B2 | 5/2004 | Geraghty |
| 6,750,048 | B2 | 6/2004 | Ruecker et al. |
| 6,768,015 | B1 | 7/2004 | Luxem et al. |
| 6,831,040 | B1 | 12/2004 | Unkefer et al. |
| 7,381,326 | B2 | 6/2008 | Haddas |
| 7,582,784 | B2 | 9/2009 | Banavali et al. |
| 7,767,837 | B2 | 8/2010 | Elliott |
| 7,868,195 | B2 | 1/2011 | Fleischer |
| 7,883,882 | B2 | 2/2011 | Franklin et al. |
| 8,404,473 | B2 | 3/2013 | Kilian |
| 2003/0199490 | A1 | 10/2003 | Antoni-Zimmermann et al. |
| 2004/0121447 | A1 | 6/2004 | Fournier |
| 2004/0161364 | A1 | 8/2004 | Carlson |
| 2004/0262219 | A1 | 12/2004 | Jensen |
| 2005/0048474 | A1 | 3/2005 | Amburgey, Jr. |
| 2005/0064577 | A1 | 3/2005 | Berzin |
| 2005/0164192 | A1 | 7/2005 | Graham et al. |
| 2005/0170479 | A1 | 8/2005 | Weaver et al. |
| 2005/0260553 | A1 | 11/2005 | Berzin |
| 2005/0273885 | A1 | 12/2005 | Singh et al. |
| 2006/0045750 | A1 | 3/2006 | Stiles |
| 2006/0101535 | A1 | 5/2006 | Forster et al. |
| 2006/0122410 | A1 | 6/2006 | Fichtali et al. |
| 2006/0166243 | A1 | 7/2006 | Su et al. |
| 2007/0102371 | A1 | 5/2007 | Bhalchandra |
| 2008/0118964 | A1 | 5/2008 | Huntley et al. |
| 2008/0120749 | A1 | 5/2008 | Melis et al. |
| 2008/0155888 | A1 | 7/2008 | Vick et al. |
| 2008/0160591 | A1 | 7/2008 | Willson et al. |
| 2008/0160593 | A1 | 7/2008 | Oyler |
| 2008/0194029 | A1 | 8/2008 | Hegemann et al. |
| 2008/0268302 | A1 | 10/2008 | McCall |
| 2008/0275260 | A1 | 11/2008 | Elliott |
| 2008/0293132 | A1 | 11/2008 | Goldman et al. |
| 2009/0011492 | A1 | 1/2009 | Berzin |
| 2009/0029445 | A1 | 1/2009 | Eckelberry et al. |
| 2009/0081748 | A1 * | 3/2009 | Oyler ............... 435/165 |
| 2009/0148931 | A1 | 6/2009 | Wilkerson et al. |
| 2009/0151241 | A1 | 6/2009 | Dressler et al. |
| 2009/0162919 | A1 | 6/2009 | Radaelli |
| 2009/0234146 | A1 | 9/2009 | Cooney et al. |
| 2009/0317857 | A1 | 12/2009 | Vick et al. |
| 2009/0317878 | A1 | 12/2009 | Champagne et al. |
| 2009/0317904 | A1 | 12/2009 | Vick et al. |
| 2009/0325270 | A1 | 12/2009 | Vick et al. |
| 2010/0022393 | A1 | 1/2010 | Vick |
| 2010/0068772 | A1 | 3/2010 | Downey |
| 2010/0151540 | A1 * | 6/2010 | Gordon et al. ............... 435/134 |
| 2010/0183744 | A1 | 7/2010 | Weissman et al. |
| 2010/0196995 | A1 | 8/2010 | Weissman et al. |
| 2010/0210003 | A1 | 8/2010 | King |
| 2010/0210832 | A1 | 8/2010 | Kilian et al. |
| 2010/0260618 | A1 | 10/2010 | Parsheh et al. |
| 2010/0261922 | A1 | 10/2010 | Fleischer et al. |
| 2010/0314324 | A1 | 12/2010 | Rice |
| 2010/0317088 | A1 | 12/2010 | Radaelli |
| 2010/0327077 | A1 | 12/2010 | Parsheh et al. |
| 2010/0330643 | A1 | 12/2010 | Kilian et al. |
| 2011/0041386 | A1 | 2/2011 | Fleischer |
| 2011/0070639 | A1 | 3/2011 | Pandit |
| 2011/0072713 | A1 | 3/2011 | Fleischer |
| 2011/0136212 | A1 | 6/2011 | Parsheh et al. |
| 2011/0196163 | A1 | 8/2011 | Fleischer |
| 2011/0197306 | A1 | 8/2011 | Bailey et al. |
| 2011/0300568 | A1 | 12/2011 | Parsheh |
| 2011/0313181 | A1 | 12/2011 | Hippler |

FOREIGN PATENT DOCUMENTS

| | | |
|---|---|---|
| JP | 2008280252 | 11/2008 |
| WO | WO2004106238 A2 | 12/2001 |
| WO | WO 2009/037683 A1 | 3/2009 |
| WO | 2011053867 | 5/2011 |

OTHER PUBLICATIONS

Janssen et al., "Enclosed outdoor photobioreactors: light regime, photosynthetic efficiency, scale-up, and future prospects," Biotechnology and Bioengineering, vol. 81, No. 2, p. 193-210, Jan. 20, 2003, Entire document, especially: Fig 4, p. 198 [online]. Retrieved from the Internet on [Oct. 5, 2010]. Retrieved from: <URL: http://onlinelibrary.wiley.com/doi/10.1002/bit.10468/pdf.

Strzepek et al., "Photosynthetic architecture differs in coastal and oceanic diatoms," Nature vol. 431, p. 689-692, Oct. 7, 2004. Entire document, especially: abstract, p. 689, col. 2; p. 691, Table 1 [online] Retrieved from the Internet on [Oct. 5, 2010]. Retrieved from: <URL: http://www.nature.com/nature/journal/v431/n7009/pdf/nature02954.pdf.

Zitelli et al., "Mass cultivation of *Nannochloropsis* sp. in annular reactors," Journal of Applied Phycology vol. 15, p. 107-113, Mar. 2003, Entire document, especially: abstract; p. 110, col. 1-2 [online]. Retrieved from the Internet on [Oct. 5, 2010]. Retrieved from: <URL: http://www.springerlink.com/content/v77772k1mp081775/fulltext. pdf.

Csogor et al., "Light distribution in a novel photobioreactor—modeling for optimization," Journal of Applied Phycology, vol. 13, p. 325-333, May 2001, Entire document, especially: Fig 2, p. 327; Table 1, p. 327; Fig 7, p. 330 [online]. Retrieved from the Internet on [Oct. 5, 2010]. Retrived from: <URL: http://www.springerlink.com/content/p77j66g3j2133522/fulltext.pdf.

Kureshy, et al. "Effect of Ozone Treatment on Cultures of *Nannochloropsis oculata, Isochrysis galbana*, and *Chaetoceros gracilis*." Journal of the World Aquaculture Society, Dec. 1999, vol. 30, No. 4, pp. 473-480; p. 473, Abstract; p. 475, "*Nannochloropsis oculata*" Section; p. 476, Table 1; p. 476, Table 2; p. 479, left column, para 2.

NCBI entry EE109892 (Jul. 27, 2006) [Retrieved from the Interenet on Oct. 19, 2009; <http://www.ncbi.nlm.nih.gov/nucest/EE109892?ordinalpos=1&itool=EntrezSystem2.PEntrez.Sequence. Sequence_ResultsPanel.Sequence_RVDocSum>].

Knuckey et al., "Production of Microalgal Concentrates by Flocculation and Their Assessment as Aquaculture Feeds," Aquacultural Engineering 35 (2006) 300-313.

Grima et al., "Recovery of Microalgal Biomass in Metabolites: Process Options and Economics," Biotechnology Advances 20 (2003) 491-515.

Lee et al. Isolation and Characterization of a Xanthophyll Aberrant Mutant of the Green Alga *Nannochloropsis oculata* Marine Biotechnology vol. 8, 238-245 (2006) (p. 239 col. 1 para 1; p. 239 col. 2 para 4; p. 240 col. 1 para 2; p. 242 col. 2 para 2; p. 241 Table 1, Fig 2; p. 242 Table 2).

Berberoglu et al. Radiation characteristics of *Chlamydomonas reinhardtii* CC125 and itstruncated chlorophyll antenna transformants tla1, tlaX and tla1-CW+. International Journal of Hydrogen Energy.2008 vol. 33 pp. 6467-6483, especially the abstract.

Ghirardi et al. Photochemical apparatus organization in the thylakoid membrane of *Hordeum vulgare* wild type and chlorophyll b-less chlorina f2 mutant. Biochimica et Biophysica Acta (BBA)—Bioenergetics. vol. 851, Issue 3, Oct. 8, 1986, pp. 331-339 (abstract only).

Steinitz et al. A mutant of the cyanobacterium *Plectonema boryanum* resistant to photooxidation. Plant Science Letters. vol. 16, Issues 2-3, Oct. 1979, pp. 327-335 (abstract only).

Koller et al. Light Intensity During Leaf Growth Affects Chlorophyll Concentration and CO2 Assimilation of a Soybean Chlorophyll Mutant. Crop Sci. 1974. vol. 14 pp. 779-782 (abstract only).

(56) References Cited

OTHER PUBLICATIONS

Shikanai et al. Identification and Characterization of *Arabidopsis* Mutants with Reduced Quenching of Chlorophyll Fluorescence. Plant and Cell Physiology, 1999, vol. 40, No. 11. pp. 1134-1142 (abstract only).

Santin-Montanaya, I. Optimal growth of *Dunaliella primolecta* in axenic conditions to assay herbicides, Chemosphere, 66, Elsevier 2006, pp. 1315-1322.

Felix, R. Use of the cell wall-less alga *Dunaliella bioculata* in herbicide screening tests, Annals of Applied Biology, 113, 1988, pp. 55-60.

Janssen, M. Photosynthetic efficiency of *Dunaliella tertiolecta* under short light/dark cycles, Enzyme and Microbial Technology, 29, 2001, pp. 298-305.

Saenz, M.E. Effects of Technical Grade and a Commercial Formulation of Glyphosate on Algal Population Growth, Bulletin of Environmental Contamination Toxicology, 1997, pp. 638-644.

Loury, Maurice Chem. Abstr., Method for rapid conversion of fats to methyl esters, Revue Francaise des Corps Gras (1967), 14 (6), 383-9. (NPL 0009).

Endo et al. "Inactivation of Blasticidin S by Bacillus Cereus II. Isolation and Characterization of a Plasmid, BSR 8, from Bacillus Cereus," The Journal of Antibiotics 41 (2): 271-2589-2601. (NPL 0015) 1987.

Hedenskog, G., et al., Investigation of some Methods for Increasing the Digestibility in Vitro of Microalgae, 1969, Biotechnology and Bioengineering, vol. XI, pp. 37-51 (NPL 0021).

Kindle et al. "Stable Nuclear Transformation of Chlamydomonas Using the Chlamydomonas Gene for Nitrate Reductase" The Journal of Cell Biology 109 (6, part 1): 2589-2601. (NPL 0024) 1989.

Prein et al. "A Novel Strategy for Constructing N-Terminal Chromosomal Fusions to Green Fluorescent Protein in the Yeast *Saccharomyces* cerevisiae" FEBS Letters 485 (2000) 29-34 (NPL 0034).

Schiedlmeier et al., "Nuclear Transformation of Volvox Carteri" Proceedings of the National Academy of Sciences USA 91(11): 5080-5084 (May 1994). (NPL 0039).

Wendland et al. "PCR-Based Methods Facilitate Targeted Gene Manipulations and Cloning Procedures" Curr.Gen. (2003) 44:115-123 (NPL 0046).

Dunstan, G.A. et al., Changes in the lipid composition and maximisatin of the polyunsaturated fatty acid content of three microalgae grown in mass culture, 1993, Journal of Applied Physiology, vol. 5, pp. 71-83.

Gouveia, L. et al., Microalgae as raw material for biofuels production, 1 Jan. 4, 2008, Journal of Industrial Microbiology & Biotechnology, vol. 36, No. 2, pp. 269-274.

Carvalheiro, F. et al., Hemicellulose biorefineries: a review on biomass pretreatments, 2008, Journal of Scientic & Industrial Research, vol. 67, pp. 849-864.

Lotero, E. et al., Synthesis of biodiesal via acid atalysis; 2005, Ind. Eng. Chem. Res., vol. 44, pp. 5353-5363.

Hallmann et al., "Genetic Engineering of the Multicellular Green Alga Volvox: A Modified and Multiplied Bacterial Antibiotic Resistance Gene as a Dominant Selectable Marker" The Plant Journal 17(1): 99-109 (Jan. 1999). (NPL 0020).

Lee et al., "Isolation and Characterization of a Xanthophyll Aberrant Mutant of the Green Alga *Nannochloropsis* oculata," Marine Biotechnology, 2006, vol. 8, pp. 238-245.

NCBI entry EE109892 (Jul. 2006) [Retrieved from the Internet on Oct. 19, 2009, ncbi.nlm.nih.gov/nucest/EE109892?ordinalops=1 &itool=EntrezSystem2.Pentrez.Sequence.Sequence_ResultsPanel.Sequence_RVDocSum>].

Berberoglu et al., "Radiation Characteristics of *Chlamydomonas* reinhardtii CC125 and its truncated chlorophyll antenna transformants tla1, tlaX, and tla1-CW+," International Journal of Hydrogen Energy, 2008, vol. 33, pp. 6467-6483.

Ghirardi et al., "Photochemical Apparatus Organization in the Thylakoid Membrane of Hordeum vulgare wild type and chlorophyll b-less chlorina f2 mutant," Biochimica et Biophysica Act (BBA)—Bioengergetics, vol. 851, Issue 3, Oct. 1986, pp. 331-339 (abstract only).

Steinitz et al., "A mutant of the *cyanobacterium* Plectonema boryanum resistant to photooxidation," Plant Science Letters, vol. 16, Issues 2-3, 1979, pp. 327-335 (abstract only).

Koller et al., "Light Intensity During Leaf Growth Affects Chlorophyll Concentration and CO2 Assimilation of a Soybean Chlorophyll Mutant," Crop Science, 1974, vol. 14, pp. 779-782 (abstract only).

Shikanai et al., "Identification and Characterization of Arabidopsis Mutants with Reduced Quenching of Chlorophyll Fluorescence," Plant and Cell Physiology, 1999, vol. 40, No. 11, pp. 1134-1142 (abstract only).

Hedenskog, G. et al., "Investigation of Some Methods for Increasing the Digestibility in Vitro of Microalgae," Biotechnology and Bioengineering, vol. XI, pp. 37-51, 1969.

Loury, "Method for Rapid Conversion of Fats to Methyl Esters," Revue Francaise des Corps Gras, 1967, 14(6), 383-389 (abstract only).

Cravotto et al., "Improved Extraction of Vegetable Oils under high-intensity Ultrasound and/or Microwaves," Ultrasonics Sonochemistry, 15: 898-902, 2008.

Ben-Amotz, Ami. "Large-Scale Open Algae Ponds," presented at the NREL-AFOSR Joint Workshop on Algal Oil for Get Fuel Production in Feb. 2008.

Ebeling et al., "Design and Operation of a Zero-Exchange Mixed-Cell Raceway Production System," 2nd Int'l Sustainable Marine Fish Culture Conference and Workshop, Oct. 2005.

Ebeling et al., "Mixed-Cell Raceway: Engineering Design Criteria, Construction, and Hydraulic Characterization," North American Journal of Aquaculture, 2005, 67: 193-201 (abstract only).

Labatut et al., "Hydrodynamics of a Large-Scale Mixed-Cell Raceway (MCR): Experimental Studies," Aquacultural Engineering vol. 37, Issue 2, Sep. 2007, pp. 132-143.

15 Kizilisoley et al., "Micro-Algae Growth Technology Systems," Presented by Selim Helacioglu, Soley Institute, 2008.

Dunstan et al., "Changes in the Lipid Composition and Maximisation of the Polyunsaturated Fatty Acid Content of Three Microalgae Grown in Mass Culture," Journal of Applied Phycology, 5, pp. 71-83, 1993.

Carvalheiro et al., "Hemicellulose Biorefineries: A Review on Biomass Pretreatments," Journal of Scientific & Industrial Research, vol. 67, Nov. 2008, pp. 849-864.

Lotero et al., "Synthesis of Biodiesel via Acid Catalysis," Ind. Eng. Chem. Res., 2005, pp. 5353-5363.

International Search Report and Written Opinion of the International Searching Authority mailed Jan. 6, 2011 for Application No. PCT/US2010/054861, filed Oct. 29, 2010.

Chen et al., "Subcritical co-solvents extraction of lipid from wet microalgae pastes of *Nannochloropsis* sp.," Eur. J. Lipid Sci. Technol., vol. 114, 2012, pp. 205-212.

Wang et al., "Lipid and Biomass Distribution and Recovery from Two Microalgae by Aqueous and Alcohol Processing," Journal of the American Oil Chemists' Society, vol. 38, Issue 2, Jul. 2011, pp. 335-345.

Pitipanapong et al.,"New approach for extraction of charantin from *Momordica* charantia with pressurized liquid extraction," Separation and Purification Technology, vol. 52, Issue 3, Jan. 2007.

Examination Report mailed Aug. 15, 2013 in Australian Application No. 2010313246 filed Oct. 29, 2010.

\* cited by examiner

SILICEOUS PARTICLES

CROSS REFERENCE TO RELATED APPLICATIONS

This application is related to U.S. patent application Ser. No. 12/485,027, filed Jun. 15, 2009, titled "Systems and Methods for Extracting Lipids from Wet Algal Biomass," the disclosure of which is incorporated herein by reference.

BACKGROUND

1. Technical Field

This application relates generally to synthesizing and utilizing materials, and more particularly to extracting and using silica-based particles.

2. Description of Related Art

Diatoms are a major group of phytoplankton. Diatoms typically form a siliceous (silica-based) frustule. As such, a bioavailable siliceous nutrient source is necessary for growth of these diatoms. Reducing the cost or energy needed to provide nutrients such as bioavailable silica may improve the economics of diatom growth, which may improve the production of substances fabricated from diatoms.

Diatoms often synthesize frustules having characteristic shapes, sizes, and structures. Frustules may be used in a variety of chemical, catalytic, optical, structural, and other applications. Such applications may benefit from improvements in extraction of frustules.

Figure 1:
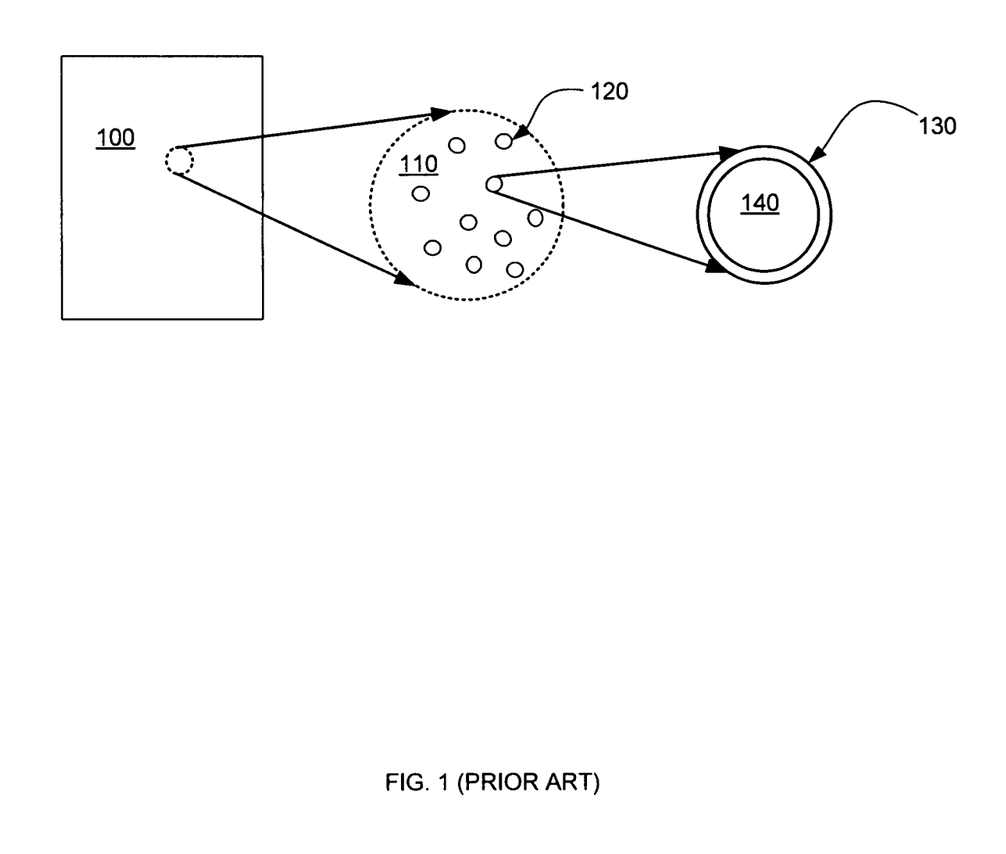
FIG. 1 is a schematic illustration of a suspension.

FIG. 1 is a schematic illustration of a suspension. Suspension 100 comprises an aqueous liquid 110 (e.g., seawater) and suspended organisms such as diatoms 120. Diatoms 120 typically include siliceous frustules 130 and a substantially non-siliceous biomass 140, which may include lipids, proteins, carbohydrates, water, and/or other components (and may include some silica).

Extraction (e.g., of lipids, frustules, and the like) may be challenging with aqueous suspensions. The effectiveness of many separation processes may be reduced when a suspension includes a substantial amount of water. Removing water (e.g., by filtering a suspended phase or evaporating the water) may require substantial energy.

SUMMARY OF THE INVENTION

Systems and methods provide for the extraction of products from a suspension. A method may include providing a suspension including an aqueous liquid and diatoms having siliceous frustules. A nonpolar solvent such as hexane may be added. The suspension and/or mixture of suspension and nonpolar solvent may be agitated (e.g., vortexed, ultrasonicated, mixed, and the like). The mixture may be segregated into two or more segregation products. Segregation may include settling, and may include centrifuging. In some embodiments, a first segregation product includes more of the frustules than a second segregation product. In some cases, the first product includes over 60% of the frustules.

In some embodiments, a first segregation product includes a majority of the frustules, and a second segregation product includes a majority of the non-siliceous biomass (e.g., lipids).

A substance (e.g., a nutrient) comprising siliceous particles may be made according to various methods. Systems and methods may include extracting nutrients (e.g., siliceous particles) from a first suspension and providing the extracted nutrients to a second suspension.

DETAILED DESCRIPTION OF THE INVENTION

Various aspects provide for extracting siliceous particles. Siliceous particles may include or be derived from diatoms. Certain embodiments provide for segregating suspensions into two or more segregation products. In some cases, a first product includes siliceous particles, and a second product may include hydrophobic species. In various embodiments, the term "hydrophobic" is used to refer to the second product, which becomes hydrophobic after agitation with the nonpolar solvent, but contains species which were not hydrophobic prior to agitation with the nonpolar solvent. For example, most of the proteins may be in the second product, but most of the proteins were not strictly speaking hydrophobic before the treatment began. Certain aspects provide for extracting non-siliceous biomass (e.g., lipids).

For the purposes of this specification, siliceous particles include particles comprising one or more silicon-containing phases, and may include silicon, silicon-oxides, silicon-hydroxides, silicon-based acids (e.g., silicic acid), silicates, polysilicates, silica-gels, opaline silica, silica-based polymers, and composites thereof. Siliceous particles may include or be fabricated from frustules. Siliceous particles may include other substances (e.g., pectin, lignin, and/or other chemicals), including sillafins and polyamines. Sillafins and polyamines are integral components of frustules, and may be more abundant than lignin or pectin.

A suspension may comprise a suspended phase and a liquid (e.g., water, seawater, growth media, and/or other liquid phases). A suspended phase may be a solid, a liquid, a composite, or another phase. In some cases, suspended phases may include small particles (e.g., less than a few mm, less than 1 mm, less than 100 microns, less than 10 microns, less than 1 micron, or even less than 100 nm). A suspended phase may include a photosynthetic organism (or a plurality thereof), such as algae, diatoms, bacteria, and the like. Some suspensions include aqueous liquids (e.g., water, seawater). Some suspensions have a concentration by mass of suspended phase in the liquid below 90%, below 80%, below 60%, below 40%, below 20%, below 10%, below 5%, below 2%, or even below 1%.

Many diatoms synthesize silica-based frustules, which may provide a source of siliceous particles. Siliceous particles may be extracted by segregating a suspension comprising the particles and removing one or more segregation products (e.g., a product containing the particles). Extraction may include extracting frustules. Many *Bacillariophyceae* (e.g., diatoms) synthesize compounds (e.g., lipids) that may be used in chemicals, fuels, and the like. Extracting may include extracting such compounds. Certain embodiments include segregating frustules into a segregation product. Some embodiments include segregating lipids into a segregation product.

Some embodiments include segregating an aqueous liquid into a segregation product. In certain embodiments, frustules are substantially segregated into a first product, lipids are substantially segregated into a second product, and water is substantially segregated into a third product. Notwithstanding that a compound may be substantially segregated into a first product, a second product may still contain an amount of the compound, typically at a concentration below (e.g., below 50% of, below 10% of, or below 1% of) that within the first compound. Segregation of a mixture into two or more segregation products may create segregation products having properties that are more suitable for subsequent processing than is the unsegregated mixture. It will be appreciated that in some cases, proteins may be almost as important as lipids a segregation product.

Figure 2:
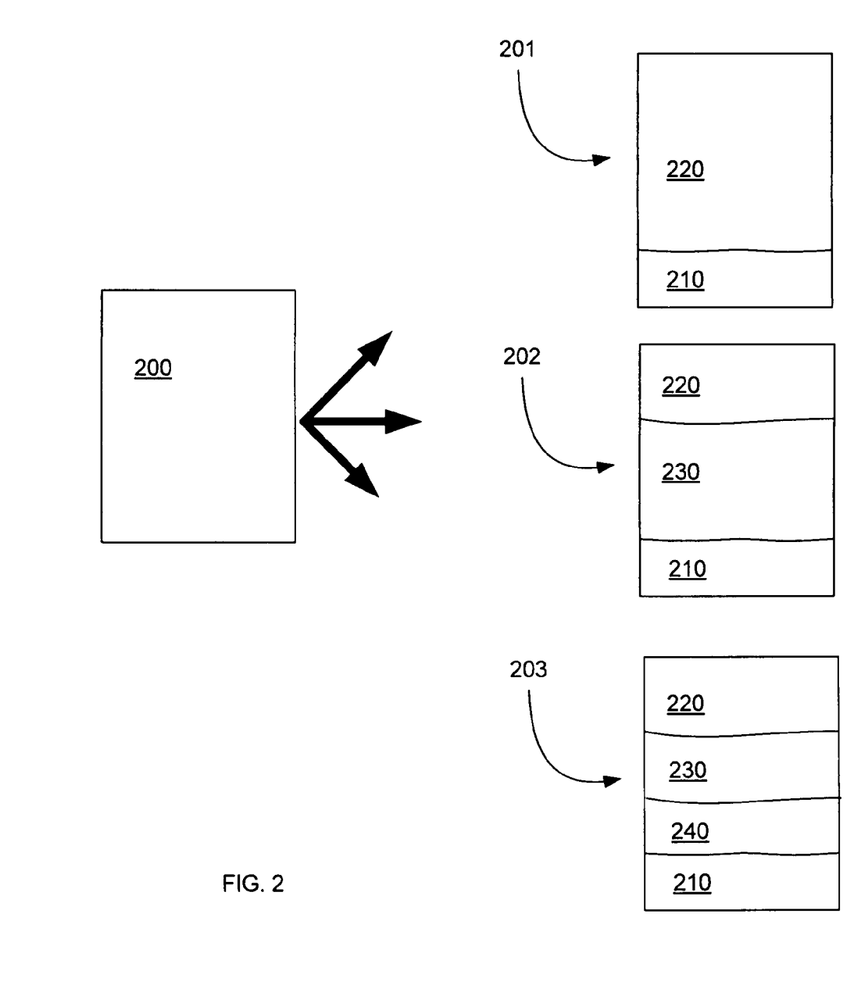
FIG. 2 illustrates several possible results of suspension segregation, according to some embodiments.

FIG. 2 illustrates several possible results of suspension segregation, according to some embodiments. Segregation of a suspension 200 into segregation products may ease the extraction of certain components, particularly components that may be preferentially segregated into a particular segregation product.

Suspension 200 may include a liquid (e.g., an aqueous liquid such as seawater) and a suspended phase. A suspended phase may include a plurality of suspended organisms, such as photosynthetic organisms. Photosynthetic organisms may include algae, bacteria, diatoms, and the like. Some photosynthetic organisms include lipids, proteins, and/or carbohydrates. Certain synthetic organisms include frustules. Additional components (e.g., a lysing agent and/or nonpolar solvent) may be added to suspension 200 to enhance segregation.

Suspension 200 may be segregated into two, three, four, five, or more segregation products. Three segregated suspensions are illustrated in FIG. 2. Segregated suspension 201 includes first product 210 and second product 220. Segregated suspension 202 includes first product 210, second product 220, and third product 230. Segregated Suspension 203 includes first product 210, second product 220, third product 230, and fourth product 240.

In some embodiments, frustules are preferentially segregated into a segregation product (e.g., first product 210). Many frustules have a density higher than that of water. In some cases, frustules are segregated at the "bottom" of a suspension (where "bottom" may be determined by gravity settling, centrifuging, and/or other acceleration). Some frustules may be bound (e.g., by the diatoms) to biomass having lower densities (e.g., lipids, proteins, carbohydrates) than the frustules. Settling of such bound frustules might be reduced or prevented by these bound "buoyant" compounds. In some embodiments, frustules are separated from these bound "buoyant" compounds (e.g., using agitation), which may enhance settling of the frustules and/or segregation of the frustules.

In some embodiments, lipids are preferentially segregated into a segregation product (e.g., second product 220). Many lipids have a lower density than water. In some cases, lipids may be segregated at the "top" of a suspension. Lipids, proteins, and carbohydrates might be bound (e.g., by the diatoms) to frustules having higher densities, which may reduce or prevent segregation of these compounds at or near the "top" of the suspension. In some embodiments, these compounds are separated from their bound frustules (e.g., using agitation), which may enhance the segregation of these compounds.

A top product and/or a lipid-containing product may also include a substantial fraction of a nonpolar solvent. In some embodiments, the intrinsic liquid component of the suspension (e.g., water) is preferentially segregated into a segregation product (e.g., third product 230). For example, segregated suspension 202 might include a first product 210 having a majority of the frustules, a second product 220 having a majority of the lipids, and a third product 230 having a majority of the aqueous liquid. "Majority" may include over 50%, over 70%, over 90%, over 95%, or even over 99%. It will be appreciated that in some cases, proteins may be almost as important as lipids a segregation product.

Certain applications may benefit from segregation that does not damage certain components. For example, extraction of proteins for use as a nutrient may require an extraction method that does not damage the protein molecules. Some applications may benefit from frustules having sizes and shapes substantially similar to their "as-synthesized" shape resulting from diatom growth, and might benefit from an extraction method that does not damage the frustules.

Some applications may benefit from a step that physically and/or chemically alters a component or compound. For example, a bioavailability of silica (sourced from frustules) may depend on particle size. Grinding the frustules may change the bioavailability (e.g., increasing the dissolution kinetics of the frustules). Some aspects provide for agitating, breaking and/or otherwise damaging the frustules and/or diatoms. Some applications of frustules may benefit from the smaller particle sizes associated with broken frustules. Certain aspects provide for modifying the particle sizes of the siliceous particles prior to extraction. Some aspects provide for modifying the particle sizes after extraction. Certain aspects include chemically separating frustules from associated diatomaceous biomass.

Figure 3:
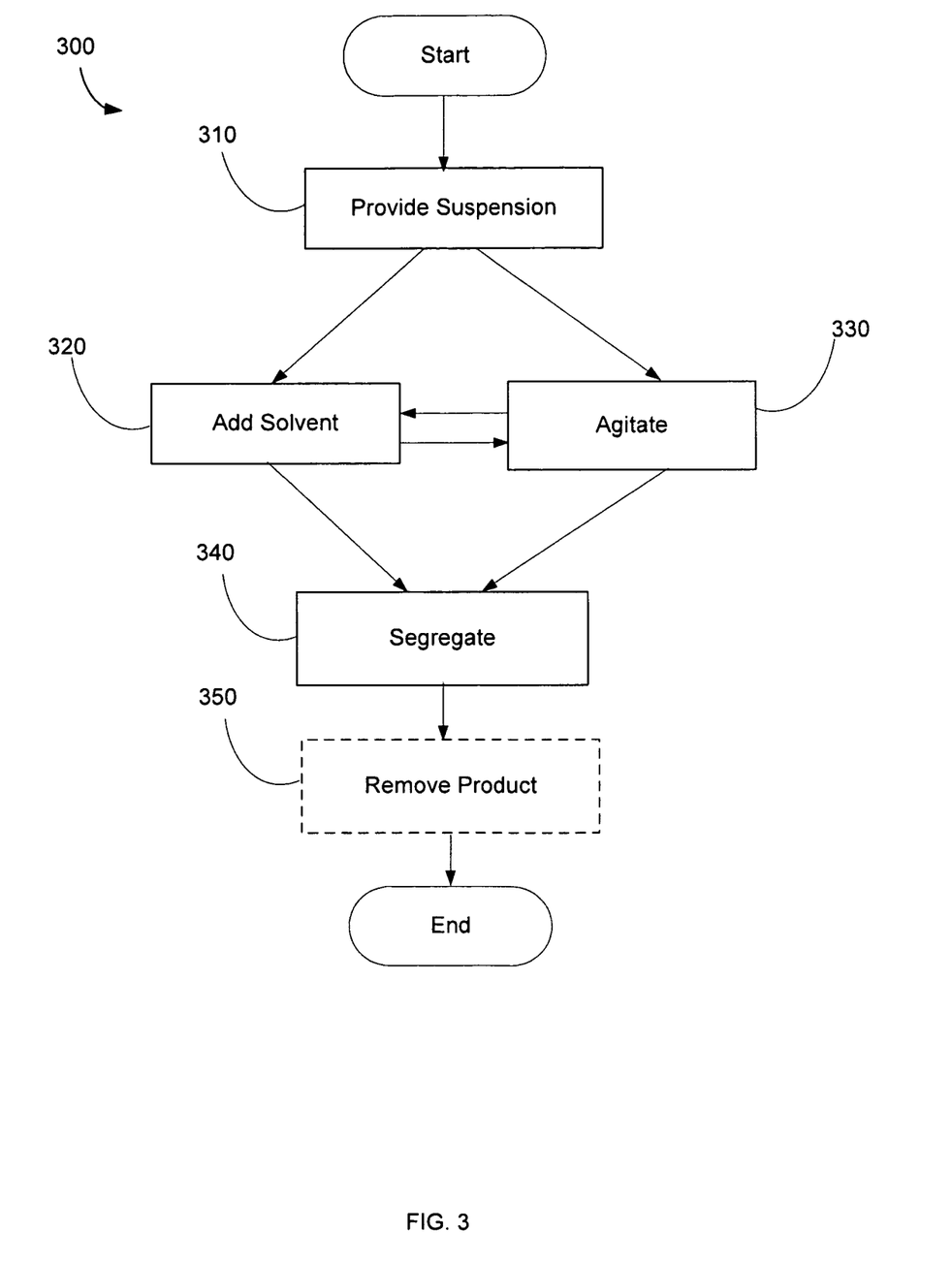
FIG. 3 illustrates a method according to some embodiments.

FIG. 3 illustrates a method according to some embodiments. Method 300 includes steps 310, 320, 330, 340, and optional step 350. A suspension is provided in step 310. The suspension may include a liquid (e.g., water, seawater, synthetic seawater, brackish water, and/or growth media) in an amount greater than 10%, 20%, 50%, 70%, 90%, or even 95% by mass as compared to the suspended phase. In some cases, the suspended phase may comprise less than 5%, or even less than 2% of the suspension. Some suspensions include diatoms suspended in (natural or synthetic) seawater. Suspensions may also include other biomass, such as lipids, which may be associated with the suspended organisms.

A nonpolar solvent may be added in step 320. According to some exemplary embodiments, the solvent may be a single chemical or a mixture of solvents. In some cases, the solvent includes one or more alkanes, esters, aldehydes, ethers, furans (e.g., THF), and/or ketones (e.g., MEK), halocarbons (e.g., TCE). Pentane, heptane, and hexane may be used as solvents. A nonpolar solvent may include a solvent that is at least partially nonpolar (e.g., various alcohols and/or acetone). A solvent may have a density below 1 g/cc, below 0.9 g/cc, below 0.8 g/cc, or even below 0.7 g/cc. Certain compounds (e.g., lipids) may dissolve in a nonpolar solvent. A nonpolar solvent with dissolved lipids may have a lower density than water, which may have a lower density than siliceous frustules.

The solvent may be added in an amount similar to the amount of the suspended biomass that interacts with the nonpolar solvent. In some cases, an amount of solvent may be within a factor of ten, a factor of five, or even a factor of two of the amount of suspended biomass (by mass). For some suspensions, an amount of nonpolar solvent may be approximately 2.5, 5, 10, 20, or even 100 times the amount of suspended biomass. In some embodiments, suspended biomass may be approximately two percent of the liquid (by mass), and an amount of nonpolar solvent may be less than 50%, 20%, 10%, 1%, or even less than 0.1% of the liquid. In one embodiment, an aqueous suspension comprises between 0.001 and 2 mass percent diatoms, and a nonpolar solvent may be added in an amount between ten and twenty times the mass of the diatoms. The suspension may be agitated in step 330. Agitation may broadly describe a variety of physical and/or chemical processes to enhance mixing and/or interaction among components of a suspension or with components added to the suspension. Agitation may include a range of applications of physical energy to the suspension. Agitation may include the application of localized mechanical forces (e.g., shear, tension, and/or compression). Agitation may include shaking, vibrating, ultrasonicating, megasonicating, and other applications of oscillatory energy. An exemplary ultrasonication of a suspension having approximately 1 liter volume may include ultrasonicating at 20 kHz using a 450 watt ultrasonic probe (Branson Ultrasonics, Danbury, Conn.) for 8 minutes. Agitation may include injecting (e.g., with jets), stirring, gas injection, gas bubble precipitation, and or other mixing (e.g., with impellers, blades, and the like). Agitation may disrupt suspended diatoms (e.g., fracture frustules), which may expose biomass within the frustules (e.g., to the solvent) and may increase the surface area of the suspended phase exposed to liquid and/or solvent. Agitation may include various chemical processes (e.g., lysing) to disrupt cell walls and/or otherwise change the chemistry of the suspension or components of the suspension. Certain embodiments that extract frustules having substantially "as-synthesized" shapes may include a greater degree of chemical agitation. Certain embodiments that extract "broken" frustules may include a greater degree of mechanical agitation. In some embodiments, a physical step may fracture frustules, and a chemical step (e.g., lysing) may disrupt cell walls. A surfactant may be added.

Temperature may be controlled (e.g., to 25° C., 75° C., 100° C., 150° C., 200° C., or even higher). Pressure may be controlled. In some cases, a pressure is maintained at a sufficiently high level (e.g., 10 psi, 50 psi, 100 psi, or even 200 psi) that an added nonpolar solvent remains liquid at temperatures above its boiling point at atmospheric pressure. Pressure and temperature may be controlled to create a supercritical fluid (e.g., supercritical $CO_2$).

Steps 320 and 330 may be performed in any order or at the same time. In some embodiments, suspensions are agitated and the solvent is be added to the agitated suspension. In some embodiments, a solvent is added and then the mixture is agitated. Solvent addition and agitation may occur at substantially the same time. Certain aspects include mixing a suspension and nonpolar solvent at a first shear rate (e.g., a low shear rate) and homogenizing or emulsifying the mixture at a second shear rate (e.g., a high shear rate). The mixture may be segregated in step 340. Segregation may separate the suspension into one or more segregation products. Segregation may include allowing the suspension to segregate using gravity (e.g., heavier products at the bottom and lighter products at the top). Segregation may be enhanced by centrifuging, for example at greater than 10×, 100×, 1000×, or even 10,000× the force of gravity (SCF).

Certain embodiments provide for segregating frustules from biomass. Agitating the frustules may expose biomass within the frustules to a nonpolar solvent and/or the aqueous liquid. Density differences between frustules, nonpolar solvents, lipids, and water may result in a segregation of frustules at the bottom of a container and nonpolar solvent and/or lipids at the top of the container.

Typically, a segregated mixture has segregation products with properties (e.g., concentration of a component) appropriate for subsequent processing and/or use. Segregation products may be removed in optional step 350. In some cases, it may be convenient to remove a top product (e.g., by decanting a product comprising lipids and nonpolar solvents). In some cases, it may be convenient to remove a bottom product (e.g., aspirating the product through a needle). A majority product may be removed (e.g., for segregated suspensions in which water is the largest component, it may be convenient to remove water first). A first product may be removed, the remaining mixture segregated or re-segregated, and a second product may be removed.

Figure 4:
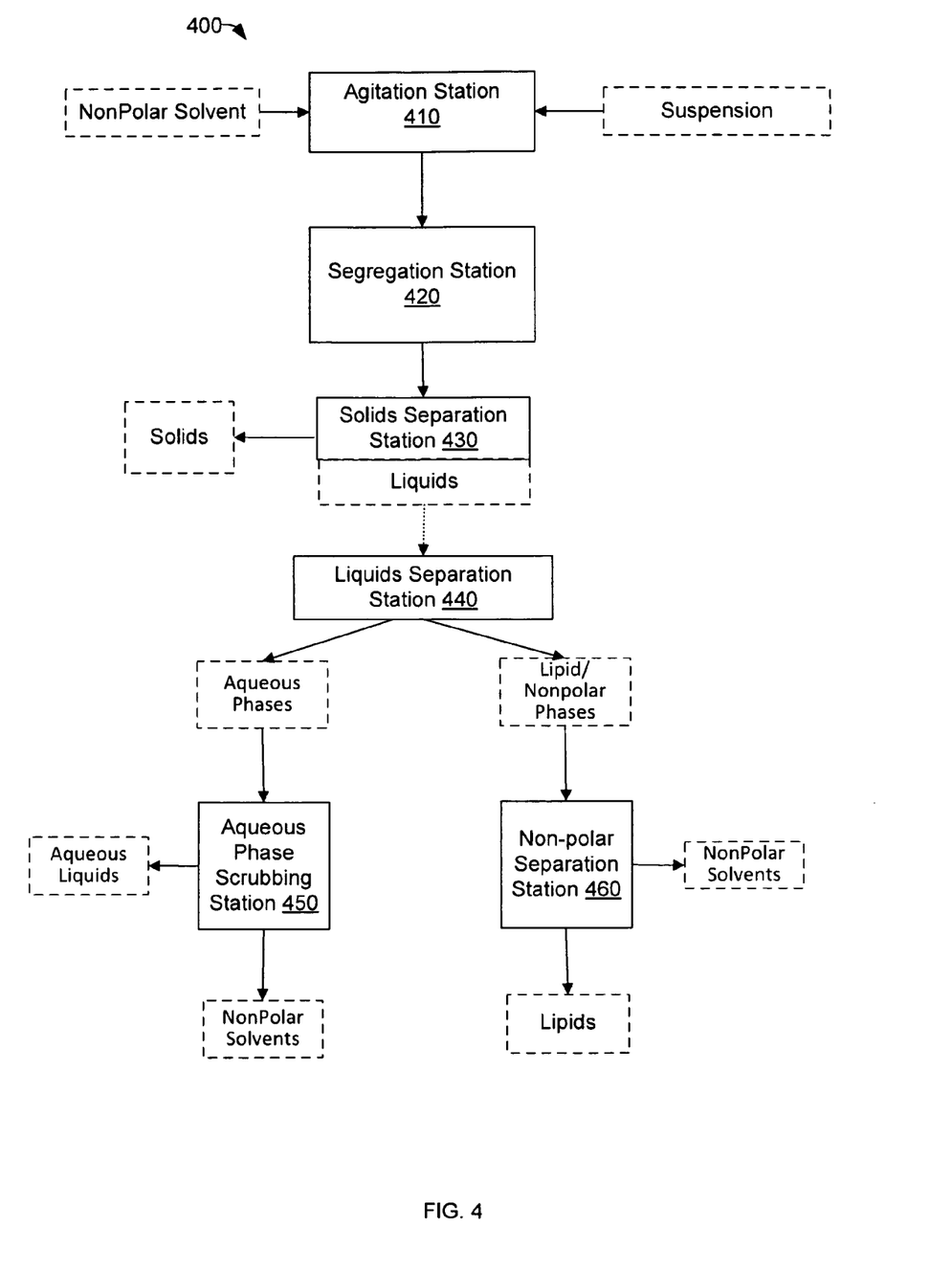
FIG. 4 illustrates several components of a system, according to some embodiments.

FIG. 4 illustrates several components of a system, according to some embodiments. In some embodiments, system 400 includes an agitation station 410, a segregation station 420, a solids separation station 430, a liquids separation station 440, an aqueous phase scrubbing system 450, and a nonpolar separation station 460. Some components may be omitted; some components may be combined.

In some embodiments, agitation station 410 receives a suspension and nonpolar solvent. Agitation station 410 may agitate the suspension and/or mixture of suspension and solvent, according to various embodiments. In some embodiments, agitation station 410 includes an ultrasonication environment and means to inject nonpolar solvent into the suspension. Agitation station 410 may include a vortexer (e.g., a blender). Means to provide an agent to enhance lysing (e.g., chalk, sand, gypsum, and the like) may be included.

The agitated mixture may pass to the segregation station 420, which segregates the mixture. In some embodiments, segregation station 420 includes a centrifuge. A segregated suspension typically includes two or more segregation products. For illustrative purposes, FIG. 4 describes facilities directed toward a mixture that may be segregated into a solids-containing segregation product and a liquids-based segregation product.

Solids separation station 430 may remove one or more products containing the majority of the solids (e.g., the frustules for a diatomaceous suspension). Liquids may be separated in liquids separation station 440, which may be integrated with solids separation station 430 in some embodiments. Liquids separation station 440 may separate liquids into substantially aqueous liquids and substantially nonpolar liquids. In some embodiments, lipids may be segregated into the nonpolar liquids. For some suspensions, aqueous and nonpolar liquids may be segregated by their mass differences, and separated using aspiration and/or decanting.

Various segregation products may include minority phases. For example, a solids-containing product may include some liquid (e.g., an aqueous liquid). An aqueous segregation product may include some nonpolar solvent, and a segregation product substantially based on the nonpolar solvent may contain some water. In some cases, minority phases may be retained with the majority phase (e.g., water may be retained with siliceous particles to form a slurry). In some cases, minority phases may be removed. Aqueous phase scrubbing station 450 may remove residual nonpolar solvents from the aqueous liquids (e.g., using distillation, such as flash distillation). Nonpolar separation station 460 may separate biomass (e.g., lipids) from nonpolar solvents, and may also separate different nonpolar solvents. Nonpolar separation station 460 may include one or more distillation apparatus.

While various aspects have been described in the context of an aqueous suspension to which a nonpolar solvent may be added, certain embodiments may be directed toward suspensions based on a nonpolar liquid to which a substantially polar solvent may be added.

Diatoms may be grown according to some embodiments. Certain aspects include providing a silica source as a nutrient for growing diatoms. In some cases, the silica source includes siliceous particles, which may include frustules and/or be derived from frustules. A method may include providing a diatom suspension and providing siliceous particles as a silica source for the diatoms. A nutrient may comprise siliceous particles, which may be suspended in an aqueous phase. In some cases, bioavailability of the silica may be monitored and/or changed. For example, monitoring a dissolved Si concentration in the liquid may be used to determine addition or subtraction of a silica source.

Certain embodiments provide for recycling frustules. Diatoms may be grown using a siliceous nutrient. Nutrients (e.g., siliceous particles) may be extracted from diatomaceous suspensions. Extracted nutrients may be recycled to additional (growing) diatoms. In some cases, recycling nutrients may reduce cost, embodied energy, pollution, and/or other aquaculture factors.

Some embodiments include sensors to sense various parameters (e.g., concentration, depth, photosynthetic rate, clarity, pH, mass, transparency, opacity, turbidity, and other characteristics). Apparatus may monitor various sensors, and systems may be actuated by automated controls (solenoid, pneumatic, piezoelectric, and the like). Some embodiments include a computer readable storage medium coupled to a processor and memory. Executable instructions stored on the computer readable storage medium may be executed by the processor to perform various methods described herein. Sensors and actuators may be coupled to the processor, providing input and receiving instructions associated with various methods. Certain instructions provide for closed-loop control of various parameters via coupled sensors providing input and coupled actuators receiving instructions to adjust parameters.

The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

What is claimed is:

1. A method for extracting siliceous particles, the method comprising:
   providing a suspension comprising an aqueous liquid and diatoms having siliceous frustules;
   adding a nonpolar solvent to the suspension to create a mixture;
   agitating the mixture;
   segregating the mixture into at least a first product and a second product, the first product having a higher amount of frustules than the second product; and
   removing any of the first and second products, wherein the second product includes lipid biomass suitable for production of biofuel, wherein a ratio of the nonpolar solvent to the diatoms is below 1 percent by mass.

2. The method of claim 1, wherein the provided suspension includes a concentration of diatoms in the liquid below 20 weight percent.

3. The method of claim 1, wherein the provided suspension includes a concentration of diatoms in the liquid below 2 weight percent.

4. The method of claim 1, wherein the liquid includes one or more dissolved salts.

5. The method of claim 1, wherein the liquid includes seawater.

6. The method of claim 1, wherein any of the diatoms includes members of the genera *Navicula, Amphora, Thalassiosira, Chaetoceros, Nitzschia, Cyclotella, Skeletonema, Phaeodactylum, Achnanthes, Coscinodiscus, Cylindrotheca, Pseudo-Nitzschia, Thalassionema, Hantzschia, Cymbella, Psammodictyon*, or any member of the Phylum *Bacillariophyta*.

7. The method of claim 1, wherein any of the diatoms includes members of the genera *Navicula, Amphora, Thalassiosira, Chaetoceros, Nitzschia, Cyclotella, Skeletonema* or *Phaeodactylum*.

8. The method of claim 1, wherein the nonpolar solvent includes an alkane.

9. The method of claim 8, wherein the alkane includes hexane.

10. The method of claim 1, wherein agitating includes ultrasonicating.

11. The method of claim 10, wherein ultrasonicating includes ultrasonicating at an energy density between 10 and 1000 watts per liter of suspension.

12. The method of claim 1, wherein segregating includes accelerating the mixture.

13. A nutrient substance made from siliceous particles fabricated according to a method comprising:
   providing a suspension comprising an aqueous liquid and diatoms having siliceous frustules;
   adding a nonpolar solvent to the suspension to create a mixture;
   agitating the mixture;
   segregating the mixture into at least a first product and a second product, the first product having a higher amount of frustules than the second product; and
   removing the first product and wherein the second product includes lipid biomass suitable for production of biofuel, wherein a ratio of the nonpolar solvent to the diatoms is below 1 percent by mass.

14. The substance of claim 13, wherein the method further comprises grinding the segregated frustules.

15. A method for providing bioavailable silica to growing organisms, the method comprising:
   providing a suspension comprising an aqueous liquid and diatoms having siliceous frustules;
   adding a nonpolar solvent to the suspension to create a mixture;
   agitating the mixture;
   segregating the mixture into at least a first product and a second product, the first product having a higher amount of frustules than the second product;
   removing the first product; and
   providing the frustules derived from the first product to the growing organisms and wherein the second product includes lipid biomass suitable for production of biofuel, wherein a ratio of the nonpolar solvent to the diatoms is below 1 percent by mass.

16. The method of claim 15, wherein providing includes dissolving the frustules in a liquid in which the growing organisms are growing.

17. A method for extracting siliceous particles, the method comprising:
   providing a suspension comprising an aqueous liquid and diatoms having siliceous frustules;
   adding a nonpolar solvent to the suspension to create a mixture;
   agitating the mixture;
   segregating the mixture into at least a first product and a second product, the first product having a higher amount of frustules than the second product; and
   removing any of the first and second products, wherein the second product includes lipid biomass suitable for production of biofuel, wherein a ratio of the nonpolar solvent to the diatoms is below 0.1 percent by mass.

18. A nutrient substance made from siliceous particles fabricated according to a method comprising:
   providing a suspension comprising an aqueous liquid and diatoms having siliceous frustules;
   adding a nonpolar solvent to the suspension to create a mixture;
   agitating the mixture;
   segregating the mixture into at least a first product and a second product, the first product having a higher amount of frustules than the second product; and
   removing the first product and wherein the second product includes lipid biomass suitable for production of biofuel, wherein a ratio of the nonpolar solvent to the diatoms is below 0.1 percent by mass.

19. A method for providing bioavailable silica to growing organisms, the method comprising:
   providing a suspension comprising an aqueous liquid and diatoms having siliceous frustules;
   adding a nonpolar solvent to the suspension to create a mixture;
   agitating the mixture;
   segregating the mixture into at least a first product and a second product, the first product having a higher amount of frustules than the second product;
   removing the first product; and
   providing the frustules derived from the first product to the growing organisms and wherein the second product includes lipid biomass suitable for production of biofuel, wherein a ratio of the nonpolar solvent to the diatoms is below 0.1 percent by mass.

* * * * *